United States Patent [19]

Brück

[11] 4,240,753

[45] Dec. 23, 1980

[54] METHOD FOR THE QUANTITATIVE DETERMINATION OF TURBIDITIES, ESPECIALLY OF IMMUNE REACTIONS

[75] Inventor: Gernot K. Brück, Cologne, Fed. Rep. of Germany

[73] Assignees: Hermann Lommel, Leverkusan; Diamant Test Gesselschaft fur Edelsteinprufungen mbH, Cologne, both of Fed. Rep. of Germany

[21] Appl. No.: 960,711

[22] Filed: Nov. 14, 1978

[30] Foreign Application Priority Data

Nov. 11, 1977 [DE] Fed. Rep. of Germany ..... 27513651

[51] Int. Cl.$^3$ ............................................ G01N 21/01
[52] U.S. Cl. ................................... 356/442; 250/575; 356/319
[58] Field of Search ................................ 356/432–439, 356/422, 319, 440; 250/565, 575, 578

[56] References Cited

U.S. PATENT DOCUMENTS

| 3,743,430 | 7/1973 | Riggs | 356/438 X |
| 3,777,173 | 12/1973 | Landrith | 250/575 |
| 3,838,925 | 10/1974 | Marks | 356/438 |

FOREIGN PATENT DOCUMENTS

| 4,080,075 | 3/1978 | Berg | 356/435 X |
| 526810 | 8/1976 | U.S.S.R. | 356/442 |

*Primary Examiner*—John K. Corbin
*Assistant Examiner*—Bruce Y. Arnold
*Attorney, Agent, or Firm*—Silverman, Cass & Singer, Ltd.

[57] ABSTRACT

A nephelometer wherein a laser beam is split to define reference and sample beams. The reference beam is directed to a photodetector and the sample beam is passed through a test sample, the emerging beam being directed to a separate photodetector. The output from the respective photodetectors are compared via a comparator, and the comparator output is divided by the reference beam photodetector output to provide a recordable signal. Preferably, the photodetectors are dispersed within Ulbrecht type spheres whereby they are indirectly irradiated by the respective beam. The invention is particularly effective for measuring turbidities of very minute degree.

34 Claims, 1 Drawing Figure

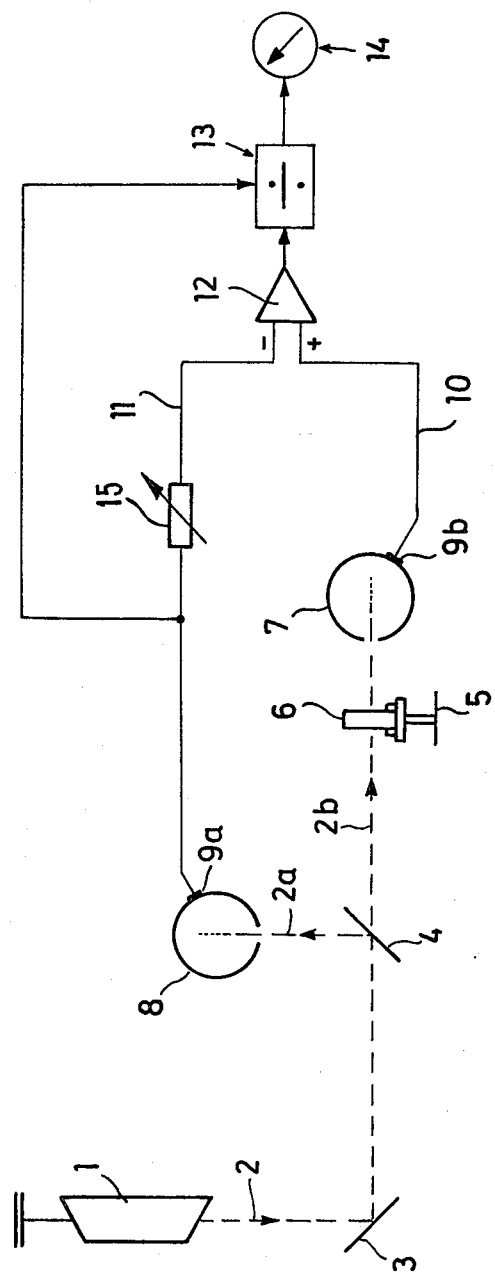

METHOD FOR THE QUANTITATIVE DETERMINATION OF TURBIDITIES, ESPECIALLY OF IMMUNE REACTIONS

The present invention relates to a method for the quantitative determination of turbidities, especially of immune reactions, for instance, for the quantitative determination of proteins including antibodies, as well as of other antigens where a test specimen is irradiated through by means of a laser beam and the light transmitted by the specimen is determined by means of a photodetector.

Several methods have been known before under the name "Laser Nephelometer". These methods are based on the principle that the scattered light emerging from the test specimen is measured and the intensity of the scattering provides information regarding the condition of the specimen which is irradiated through. With a well-known method having a light trap behind the test specimen, the nonscattered center portion of the light beam is masked out and only the scattered portion is determined in the narrow zone around the central light beam. With this method, the accuracy of measurement is impaired by the granular noise of the electronics in the case test specimens which cause only slight scattering. Another method measures only the scattered light emerging at a certain angle; however, the generated signal must be amplified here by means of a photoelectric multiplier because of its slight strength. However, this necessitates considerable circuit expenditures and, moreover, test specimens which scatter light only weakly can be examined by this method only with difficulty, since the measuring signal can be degraded by the noise of the photoelectric multiplier. Both well-known methods have another disadvantage in common, namely, that fluctuations in the laser beam intensity limit the accuracy of measurement, especially in the case where slight concentrations of the components are to be determined.

The present invention is based on the problem of developing a method which makes possible a high accuracy of measurement for any concentration of the test specimen, especially where very small concentrations are to be determined, such as in specimens having slight turbidity as well as determinations involving high concentrations of the components, the normally encountered inaccuracies are eliminated by fluctuation in the intensity of the laser beam.

As defined in the herein invention, this is achieved by the fact that the change in the intensity of the beam emerging from the test specimen compared to the entering intensity is measured and that this measured value is compared with a reference intensity value obtained from the light beam before it enters the specimen, and that the value resulting therefrom is given off as an output signal.

Accordingly, the change in the intensity of the entire measuring beam which passes through the test specimen, caused by the scattering of the light, as for example on complex-forming particles of the test liquid, is measured and simultaneously compared with a reference value of a determined light intensity which is taken from the light beam emitted by the laser. Since the reference value and the measuring beam passing through the test specimen originate from the same light source, i.e. the same laser, fluctuations in the intensity cannot influence the measuring result, because they occur simultaneously in the reference beam and in the measuring beams. Thus the ratio from the differential value of these two beams and the reference beam, which is preferably processed further into the measuring result, is not affected by such fluctuations. From this there results also a great sensitivity of the method as defined in the invention since a sufficient output signal results even with test specimens which scatter light only slightly.

In an advantageous development of the invention, the laser beam is divided into two partial beams, the reference beam and the measuring beam—preferably 50:50—in order to obtain the reference value. Accordingly, the method as defined in the invention works according to a two-beam principle in contrast to the well-known methods carried out according to the single-beam principle. As defined in the invention, it is also expedient if the measuring of the intensity of the measuring beam emerging from the test specimen and that of the reference value or the reference light beam, respectively, is carried out by means of photodetectors. Preferably each of the two partial beams are led first into a respective Ulbricht sphere-type photometer before being measured by the respective photodetector. This measuring principle is advantageous in that the detectors are not irradiated directly by a beam; thereby, inaccuracies of measurement are avoided.

A laser having a short wavelength in the visible range, especially in the range of 400 to 650 nm, is used advantageously as a light source. For, in connection with the short wavelengths, a high scattering intensity is to be expected because the scattering increases by the fourth power of the frequency of the light falling in. In the case of shorter wavelengths, one can work with lesser concentrations of the components to be determined without the accuracy of measurement of the method as defined in the invention suffering very much thereby.

Since the method as defined in the invention operates on a high energy level in contrast to well-known methods with exclusive measuring of the scattered light, a high amplification factor for the output signal is not required so that a high signal-noise ratio can be obtained and great sensitivity achieved.

The single FIGURE in the drawings is a schematic flow representation of an embodiment of the invention.

The device employs a monochromatic laser as a light source. The laser preferably is rotation-polarized and has an operating range at a wavelength of approximately 633 nm. As shown, the coherent light beam 2 emitted by laser 1 falls on a deflecting mirror 3, namely at an angle of incidence of 45°. The deflecting mirror 3 is reflective particularly for the respective wavelength used so that the light beam 2 reflecting from mirror 3 falls on a beam divider plate 4. Preferably plate 4 may be a semi-transparent mirror—where the light beam is divided into beams 2a and 2b at a ratio of division of about 50:50. The partial beam 2a serves as a reference beam and the partial beam 2b serves as a measuring beam. The measuring beam 2b falls onto a test specimen 6 such as an antigen-antibody complex contained in a specimen holder 5. The light emerging from the test specimen 6 is received by an Ulbricht sphere-type photometer 7. In the Ulbricht sphere-type photometer 7, there is a photodetector 9b which receives the light entering the Ulbricht sphere-type photometer 7 and transforms it into an electrical signal.

The reference beam 2 also is led into an Ulbricht sphere-type photometer 8. The intensity of the light of reference beam 2 is determined by a photodetector 9a and transformed into an electrical signal. The electrical output signals of the photodetectors 9a and 9b are transmitted to the two inputs of a sum-and-difference amplifier 12 by way of electrical lines 10 and 11. A variable resistor 15 is inserted between the reference detector and the amplifier 12. The actual measured value is then obtained from the difference signal and from the reference signal by quotient formation by means of a quotient amplifier 13 and can then be put out on any display device 14, such as a digital display or a printer. By way of example, display device 14 can indicate the percentage value of the absorption. The device as defined in the invention is constructed so that the paths of the rays 2, 2a and 2b are closed off from the exterior to prevent light leakage thereinto. The method and the device of the invention can be used for measuring absorption as well as the transmission, and particularly are useful for diagnostic and scientific application in laboratory medicine such as in the performance of blood tests such as blood coagulation determinations.

The present invention also can be advantageously employed for measuring the pollution in stagnant and flowing waters.

I claim:

1. A method for quantitative determination of very minute degrees of turbidities in a dilute test specimen comprising the steps of:
   a. irradiating a test specimen with a monochromatic laser beam along a first path;
   b. detecting and measuring the intensity of the laser beam emerging from the test specimen to provide a first measurement signal;
   c. diverting a defined portion of the laser beam from said first path to a lateral path prior to interception of said beam by the test specimen;
   d. detecting the intensity of said diverted laser beam along the lateral path to provide a reference signal;
   e. subtracting said reference signal from said first signal to provide an output signal;
   f. dividing said output signal by said reference signal to provide a quotient output signal corresponding to the true differential without variation effects originating with the laser light source; and,
   g. responding to said quotient output signal to provide a value for turbidity.

2. The method as claimed in claim 1 in which the said diverted portion of the laser beam and the laser beam emerging from the test specimen are each received by a respective photoresponsive element offset from the direct path of each respective beam so as to be activated by indirect, uniform irradiation of each respective beam.

3. The method as claimed in claim 2 wherein the diverted beam and the emerging beam are each introduced directly into a respective sphere having a uniform inner reflective surface and an entrance aperture and wherein the photoresponsive detector is positioned at the reflective surface and offset from the direct irradiation by the respective beam.

4. The method as claimed in claim 3 in which said laser beam is rotation polarized.

5. The method as claimed in claim 2 wherein the reference beam and the emerging beam are each measured by an indirectly irradiated photodetector directly irridiated by the respective beam.

6. The method as claimed in claim 2 in which the diverted beam intensity has a predetermined ratio relative to the beam intensity irradiating said test sample.

7. The method as claimed in claim 2 in which said laser beam is rotation polarized.

8. The method as claimed in claim 2 in which the ratio of the diverted beam intensity to the beam intensity which irradiates the test sample is about 50:50.

9. The method as claimed in claim 2 wherein said laser beam wavelength is in the visible range.

10. The method as claimed in claim 1 in which the diverted beam intensity has a predetermined ratio relative to the beam intensity irradiating said test sample.

11. The method as claimed in claim 10 in which the ratio of the diverted beam intensity to the beam intensity which irradiates the test sample is about 50:50.

12. The method as claimed in claim 11 in which said laser beam is rotation polarized.

13. The method as claimed in claim 11 wherein the reference beam and the emerging beam are each measured by an indirectly irradiated photodetector directly irridiated by the respective beam.

14. The method as claimed in claim 11 wherein said laser beam wavelength is in the visible range.

15. The method as claimed in claim 1 wherein the diverted beam and the emerging beam are each introduced directly into a respective sphere having a uniform inner reflective surface and an entrance aperture, and wherein the photoresponsive detector is positioned at the reflective surface and offset from the direct irradiation by the respective beam.

16. The method as claimed in claim 15 in which said laser beam is rotation polarized.

17. The method as claimed in claim 15 wherein the reference beam and the emerging beam are each measured by an indirectly irradiated photodetector directly irridiated by the respective beam.

18. The method as claimed in claim 15 wherein said laser beam wavelength is in the visible range.

19. The method as claimed in claim 1 in which the ratio of the diverted beam intensity to the beam intensity which irradiates the test sample is about 50:50.

20. The method as claimed in claim 1 in which said laser beam is rotation polarized.

21. The method as claimed in claim 1 wherein said laser beam wavelength is in the visible range.

22. The method as claimed in claim 1 wherein the reference beam and the emerging beam are each measured by an indirectly irradiated photodetector as opposed to a photodetector directly irradiated by the respective beam.

23. The method as claimed in claim 22 in which said laser beam is rotation polarized.

24. The method as claimed in claim 23 wherein the wavelength of said laser beam is selected to be in the range of 400 to 650 nanometers.

25. The invention as claimed in claim 24 in which the signal dividing device is a quotient amplifier.

26. The invention as claimed in claim 25 in which each of the detectors comprises an Ulbricht sphere type photometer having an entrance for receiving the beam and a photoresponsive device responsive to radiation in the interior of the sphere at a location offset from direct radiation of the beam.

27. A device for quantitative determination of very minute degrees of turbidity in a dilute biological specimen or the like which comprises A. a laser light source arranged to provide a monochromatic laser beam along a first beam path;
B. a specimen holder in the said path adapted to have the specimen disposed therein, the walls of said holder being substantially transparent to the laser beam;
C. a first photoresponsive detector aligned with said path and disposed to receive the portion of the beam which has passed through the specimen holder directly and to provide a measurement signal as its output;
D. a beam splitter in the path but before the specimen holder adapted to divert a substantial portion of the original beam along a lateral path;
E. a second photoresponsive detector disposed to receive the portion of beam of said lateral path directly and provide a reference signal as its output;
F. a differential amplifier having two inputs and an output channel;
G. each detector having an output terminal which is connected to a different input of the differential amplifier;
H. a signal dividing device connected to the output channel of the differential amplifier;
I. the second detector also having its output connected to said signal dividing device and arranged so that the differential amplifier output is divided by the second detector output in order to provide a quotient output that corresponds to the true differential without the variation effects of said laser light source; and,
J. means for responding to said quotient output.

28. The invention as claimed in claim 27 in which each of said detectors is of the type which has a photoresponsive element out of the path of its received incident beam and is activated by indirect, uniform irradiation of said incident beam as opposed to being directly irradiated by the respective beam.

29. The invention as claimed in claim 28 in which the signal dividing device is a quotient amplifier.

30. The invention as claimed in claim 29 in which each of the detectors comprises an Ulbricht sphere type photometer having an entrance for receiving the beam and a photoresponsive device responsive to radiation in the interior of the sphere at a location offset from the direct path of the beam.

31. The invention as claimed in claim 27 and means for shielding said beam paths to protect them from light entering from the exterior of said device.

32. The invention as claimed in claim 31 in which each of the detectors comprises an Ulbricht sphere type photometer having an entrance for receiving the beam and a photoresponsive device responsive to radiation in the interior of the sphere at a location offset from the direct path of the beam.

33. The invention as claimed in claim 27 in which said beam splitter is a semi-transparent mirror.

34. The invention as claimed in claim 27 in which the beam provided by said laser light source is polarized.

* * * * *